United States Patent
Donnelly et al.

(10) Patent No.: US 12,121,671 B2
(45) Date of Patent: Oct. 22, 2024

(54) INTERMITTENT CATHETER

(71) Applicant: ConvaTec Limited, Flintshire (GB)

(72) Inventors: David Donnelly, Flintshire (GB); Jarrod D'Annibale, Erie, PA (US); Tony Dedionisio, Erie, PA (US); Jason Bryant, Erie, PA (US)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 18/492,135

(22) Filed: Oct. 23, 2023

(65) Prior Publication Data
US 2024/0042167 A1 Feb. 8, 2024

Related U.S. Application Data

(63) Continuation of application No. PCT/GB2022/051019, filed on Apr. 22, 2022.

(30) Foreign Application Priority Data

Apr. 23, 2021 (GB) .................................. 2105827

(51) Int. Cl.
*A61M 25/00* (2006.01)
(52) U.S. Cl.
CPC .... *A61M 25/0017* (2013.01); *A61M 25/0045* (2013.01)
(58) Field of Classification Search
CPC ............ A61M 25/0017; A61M 25/002; A61M 25/0111; A61M 2210/1085; A61M 2210/1092; A61M 25/0097; A61M 2025/0175; A61M 25/0113; A61M 25/0169; A61M 25/0606; A61M 2202/0496
See application file for complete search history.

(56) References Cited

U.S. PATENT DOCUMENTS

| | | | | |
|---|---|---|---|---|
| 4,170,996 A | * | 10/1979 | Wu ..................... | A61M 25/002 604/171 |
| 2001/0001443 A1 | * | 5/2001 | Kayerod ............... | A61L 29/085 206/364 |
| 2004/0158231 A1 | * | 8/2004 | Tanghoj ............ | A61M 25/0067 604/544 |

(Continued)

FOREIGN PATENT DOCUMENTS

| | | | | |
|---|---|---|---|---|
| GB | 2402070 A | * | 12/2004 | ........ A61M 25/0017 |
| WO | 2006092150 A1 | | 9/2006 | |

(Continued)

OTHER PUBLICATIONS

International Preliminary Report on Patentability; International Application No. PCT/GB2022/051019; dated Jul. 27, 2017; 8 pages.

(Continued)

*Primary Examiner* — Adam Marcetich
(74) *Attorney, Agent, or Firm* — TAFT STETTINIUS & HOLLISTER LLP; Ryan O. White; Derek B. Lavender

(57) ABSTRACT

Described is a catheter arrangement in which a sealed container of wetting agent is provided in a housing cap. The sealed container is pierced with a piercing member such that the wetting agent is directed towards the catheter. The wetting agent may bypass a handling surface of the catheter whilst being directed to the catheter tube.

19 Claims, 2 Drawing Sheets

(56) References Cited

U.S. PATENT DOCUMENTS

| | | | | |
|---|---|---|---|---|
| 2007/0225649 A1* | 9/2007 | House | A61M 25/002 | 604/171 |
| 2008/0091136 A1* | 4/2008 | House | A61M 25/002 | 604/23 |
| 2008/0260576 A1* | 10/2008 | Bruun | A61M 25/0111 | 206/364 |
| 2010/0116695 A1* | 5/2010 | Bezou | A61M 25/002 | 206/210 |
| 2010/0258568 A1* | 10/2010 | Frederiksen | A61M 25/0111 | 53/474 |
| 2011/0160704 A1* | 6/2011 | Park | A61M 25/0111 | 604/528 |
| 2012/0289942 A1* | 11/2012 | Becker | A61M 25/002 | 53/428 |
| 2016/0015929 A1* | 1/2016 | Tanghoej | A61F 5/44 | 604/544 |
| 2016/0339205 A1* | 11/2016 | Foley | A61M 25/002 | |
| 2018/0169377 A1* | 6/2018 | Hickmott | A61M 25/0097 | |
| 2021/0138189 A1* | 5/2021 | Montes de Oca | A61M 25/0017 | |
| 2021/0178117 A1* | 6/2021 | McDonnough | A61M 39/10 | |
| 2021/0290894 A1* | 9/2021 | Palmer | A61M 25/0017 | |
| 2021/0290895 A1* | 9/2021 | Nielsen | A61M 25/0017 | |
| 2022/0296355 A1* | 9/2022 | Göbel | A61M 25/0102 | |

FOREIGN PATENT DOCUMENTS

| | | |
|---|---|---|
| WO | 2009068043 A2 | 6/2009 |
| WO | 2009140971 A1 | 11/2009 |

OTHER PUBLICATIONS

Written Opinion of International Preliminary Examining Authority; International Application No. PCT/GB2022/051019; dated Feb. 13, 2023; 8 pages.

* cited by examiner

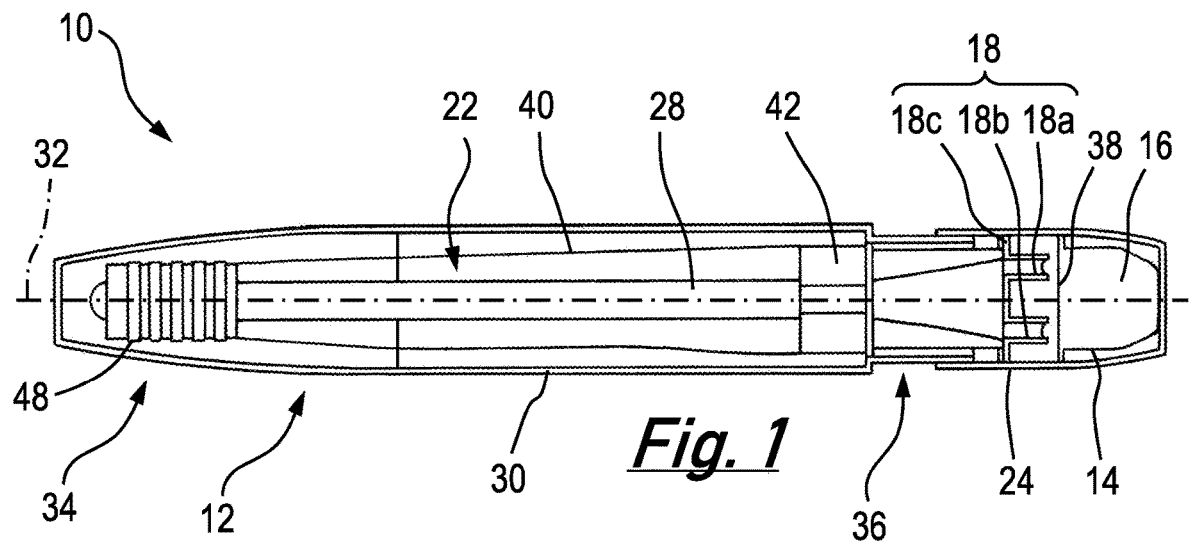
*Fig. 1*
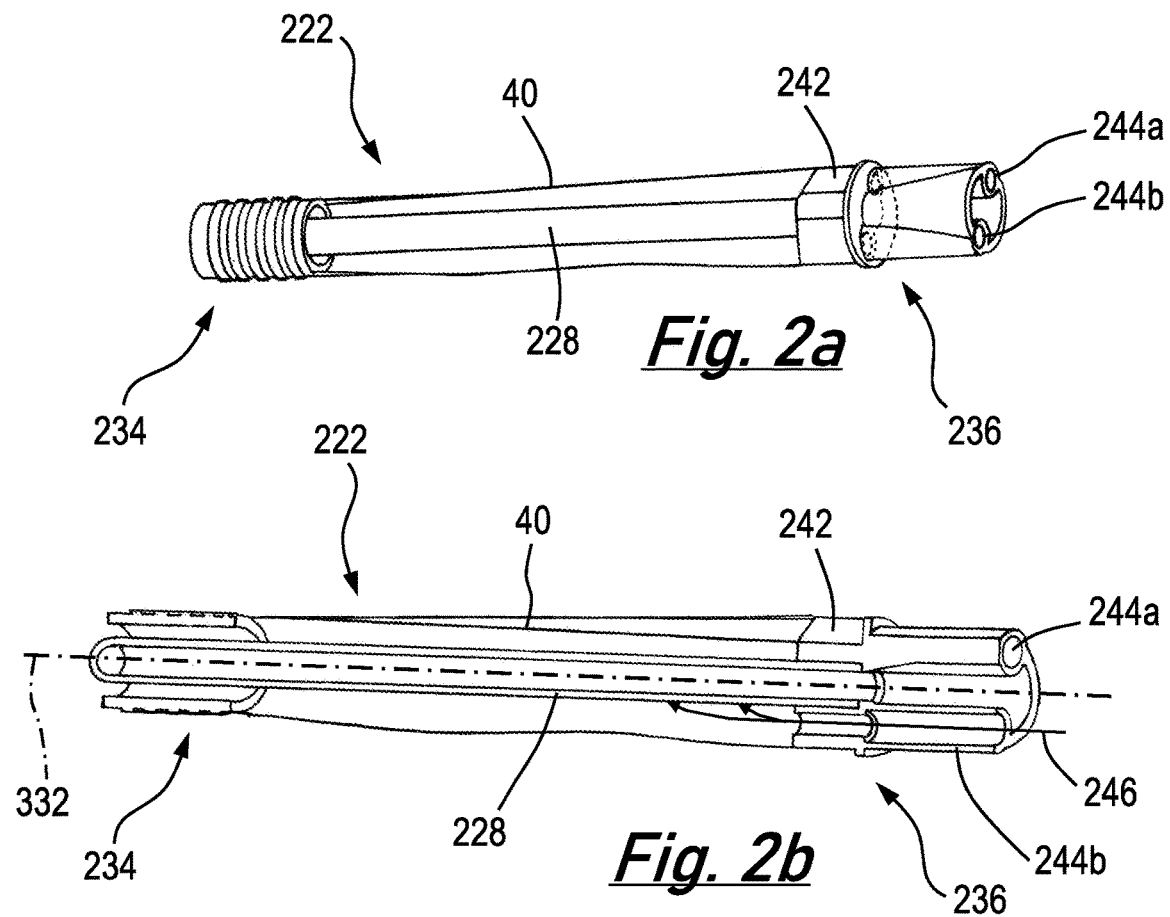
*Fig. 2a*
*Fig. 2b*

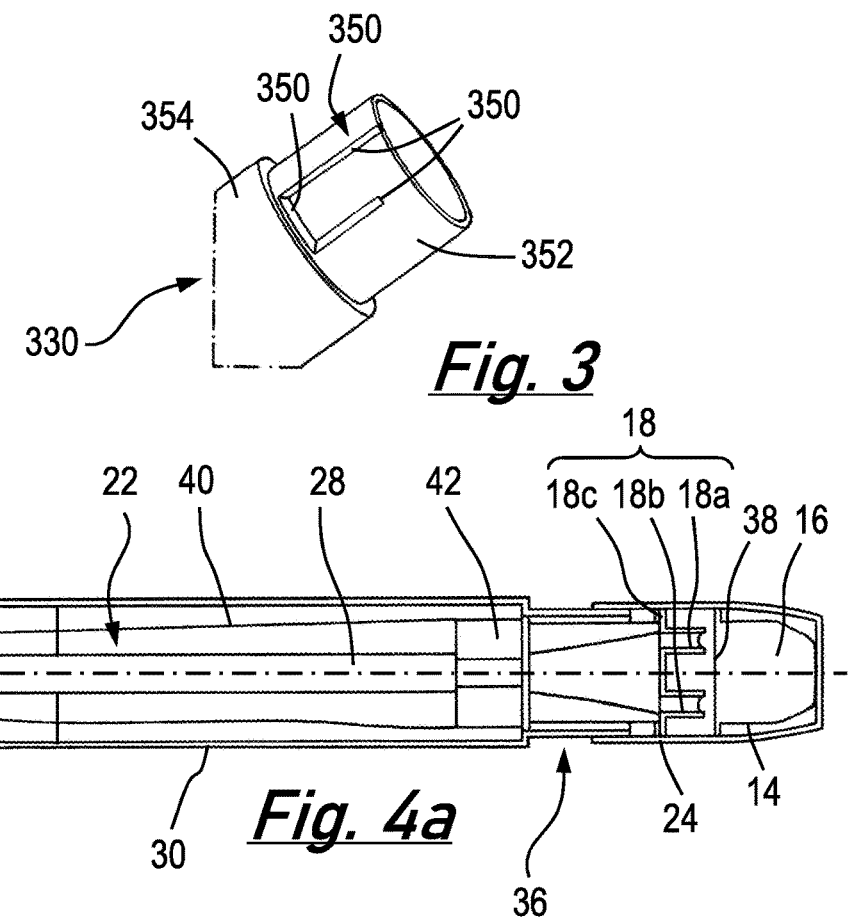
Fig. 3
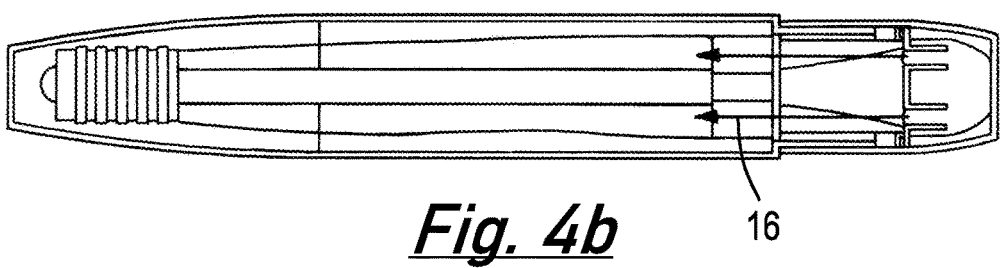
Fig. 4a
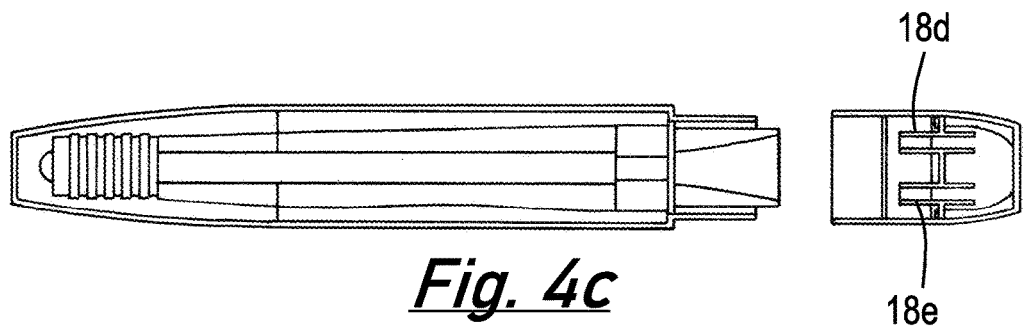
Fig. 4b
Fig. 4c

INTERMITTENT CATHETER

TECHNICAL FIELD OF THE INVENTION

The present invention relates to an intermittent catheter (e.g. a urinary catheter).

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc. remain open. Urinary catheters are designed for use for insertion into a user's bladder via the urethra to drain the bladder.

To maximise comfort and minimise the risk of trauma and/or infection, an outer surface of the catheter tube is typically wetted using a wetting agent prior to insertion by the user. In further developments, the catheter tube itself comprises, is integrated with or is coated with a hydrophilic component (e.g. a hydrophilic polymer) which serves to reduce friction further upon application of the wetting agent.

Some catheters may be supplied pre-wetted in a packaging, for instance, where the catheter is at least partially submerged within wetting agent within the packaging. Whilst this may ensure the catheter tube is adequately wetted prior to use, such arrangements suffer in that components of the catheter other than the catheter tube such as a gripper element or funnel can also become wetted. This has a detrimental effect of the experience of the user where it may become difficult to hold and direct the catheter tube as required. This is particularly problematic where the user is performing self-catheterisation. Further, having the catheter submerged may effectively reduce the shelf-life of the catheter due to long-term exposure of components of the catheter to moisture.

It is therefore seen advantageous to provide a catheter which may be wetted at or immediately prior to the point of use.

In an attempt to address this, some catheters are provided in packaging which includes a rupturable container or sachet within the packaging which a user may burst to release the wetting agent. Typically, this involves the user squeezing the packaging to cause the container/sachet to break. However, such arrangements experience similar problems to those discussed above where the wetting agent is allowed to come into contact with other components of the catheter. Such arrangements also result in the possibility of the catheter tube not being fully wetted, or indeed wetted at all, prior to use. This can be harmful for the user.

It is therefore advantageous to provide a catheter which includes a means of supplying a wetting agent solely to the catheter tube to improve user experience.

In further prior art solutions, the catheter may be packaged within a packaging which includes a wetting device. In use, the catheter tube may be moved through the wetting device as the catheter is removed from the packaging and in doing so wetting the catheter tube. Examples of such catheters are shown in PCT application No. PCT/IB2018/001539 in the name of Convatec Limited.

However, due to packaging constraints the amount of wetting agent able to be contained in such wetting devices is low, and there therefore remains a possibility of the catheter tube not being fully wetted in such solutions, especially where the catheter is near the end of its shelf life and some of the solution may have evaporated.

For mechanisms which wet the catheter tube from the distal end, an insufficient volume of wetting agent may result in the tip end not being wetted at all which is undesirable since the tip end will be introduced into the urethra first and is hence most likely to cause injury if inadequately wetted before use.

Further a minimum length of catheter is required for regulatory approval and it is desirable to ensure that the length is wetted with a minimum impact on the packaging size.

It is an aim of an embodiment or embodiments of the invention to overcome or at least partially mitigate one or more problems with the prior art and/or to provide an improved intermittent catheter.

SUMMARY OF THE INVENTION

The present invention provides a catheter assembly according to the appended claims.

One broad aspect of the invention provides a catheter assembly comprising a cap; the cap containing wetting agent, and at least one piercing member configured to pierce the sealed container and direct the wetting agent to the catheter tube.

The catheter assembly may comprise an external housing. The external housing may comprise a cap. The cap may comprise a sealed container of wetting agent. The cap may be configured to move from a first position to a second position. The catheter assembly may further comprise a catheter comprising a catheter tube. In the second position the piercing member may be configured to pierce the sealed container and direct the wetting agent to the catheter tube.

Accordingly one aspect of the invention provides a catheter assembly comprising: an external housing, the external housing comprising a cap; the cap comprising a sealed container of wetting agent, wherein the cap is configured to move from a first position to a second position; the catheter assembly further comprising at least one piercing member; and a catheter comprising a catheter tube, wherein in the second position the piercing member is configured to pierce the sealed container and direct the wetting agent to the catheter tube.

Providing a sealed container within the cap provides a convenient location for the sealed container which is easy to load during an assembly of the device and provides ample space for a required volume of liquid to be stored. Further, the provision of the sealed container in the cap allows the sealed container to be pierced during the removal of the cap, by incorporating a piercing movement into the removal procedure.

Another broad aspect of the invention provides a catheter assembly comprising a cap; the cap containing wetting agent; and a catheter having a catheter tube and an outlet end; the catheter assembly comprising at least one fluid passageway configured to direct the wetting agent to an external surface of the catheter tube bypassing an exterior handling surface of the outlet end of the catheter.

The catheter assembly may comprise an external housing. The external housing may comprise the cap. The cap may comprise a sealed container of wetting agent. The catheter assembly may comprise a piercing member. The cap may be configured to move from a first position to a second position. The outlet end may have an exterior handling surface and an interior main flow passage.

Accordingly, in another aspect, the present disclosure may provide a catheter assembly comprising: an external housing, the external housing comprising: a cap, the cap comprising a sealed container of wetting agent; and, a piercing member, wherein the cap is configured to move from a first position to a second position; the catheter assembly further comprising: a catheter comprising a catheter tube and an outlet end, the outlet end having an exterior handling surface and an interior main flow passage; and, at least one fluid passageway configured to direct the wetting agent to an external surface of a catheter tube bypassing the exterior handling surface of the outlet end.

Providing at least one fluid passageway which bypasses the exterior handling surface of the outlet end of the catheter prevents the handling surface becoming wet when the catheter is being prepared for use. This can improve the user experience and allow the gripability of the handling surface to be maintained.

Optional features of the above referenced aspects are now provided. It will be appreciated that, except where mutually exclusive, the optional features may be applied to any aspect and in any possible combination.

Moreover, the catheter assembly may comprise the features of any combination of the aspects outlined above, e.g. it may include at least one piercing member configured to pierce the sealed container and direct the wetting agent to the catheter tube; and at least one fluid passageway configured to direct the wetting agent to an external surface of the catheter tube bypassing an exterior handling surface of the outlet end.

The catheter may be a female intermittent catheter. The catheter may have a length of between 9 and 20 cm; it may have a length of between 120 and 200 mm; it may have a length of between 10 and 15 cm, or, for example, between 140 mm and 155 mm. The catheter assembly may have a length of 10 and 25 cm; it may have a length of between 11 and 16 cm, for example, between 150 mm and 165 mm.

The catheter tube may be functionalised. For example it may comprise, be integrated with or be coated with a hydrophilic component (e.g. a hydrophilic polymer). The hydrophilic component serves to reduce friction further upon application of the wetting agent. At least an external surface of the catheter tube may be functionalised, e.g. the hydrophilic component may be provided on at least an external surface of the catheter tube (which is in contact with the urethra in use).

The external housing may further comprise a main body in which the catheter tube is at least partially arranged. The cap may be detachably attached to the main body.

The catheter may comprise a main flow passage for the passage of urine. The main flow passage may extend along and define a longitudinal axis of the catheter. The main flow passage may be provided by a wall of catheter tube. The main flow passage may have a proximal inlet at an insertion end of the catheter, and a distal outlet.

The piercing member may further comprise one or more fluid passageways for bypassing the catheter outlet such that the wetting agent is directed to an external surface of the catheter tube. The one or more fluid passageways may be referred to as bypass channels in some embodiments disclosed herein. The catheter outlet may comprise an external handling surface which is handled by a user for removing the catheter from the housing, and for inserting the catheter during use. The fluid passageways may bypass the external handling surface.

The piercing member may comprise one or more lances which extend rearwards (i.e. distally) of the catheter outlet and be distal-most in relation to the catheter. The one or more lances may comprise the fluid passageways (in part or full). The lances may be hollow comprising a through passage which extends from with the sealed container when pierced to an outlet which is located distally of the terminal end of the catheter so as to direct the wetting agent to an external surface of the catheter tube.

The one or more fluid passageways may be arranged radially outside of a longitudinal axis of the main flow passage. Hence, the main flow passage is generally radially inwards of the wetting agent fluid passageways such that the wetting agent is directed radially outwards of the main flow passage in an axially extending direction.

The catheter may comprise the one or more fluid passageways (e.g. a portion of the one or more fluid passageways). The catheter may comprise an outlet body. The outlet body may incorporate the terminal end of the catheter tube. The outlet body may comprise the external handling surface of the catheter. The outlet body may comprise at least part of the main flow passage (for passage of urine). The outlet body may comprise one or more flow enhancing features for aiding the flow from catheter tube. The one or more flow enhancing features may comprise a funnel, for example.

A portion of the one or more fluid passageways may be provided by the catheter. The one or more fluid passageways may be integrally formed in the catheter. The one or more fluid passageways may be integrally formed in the outlet body of the catheter. The one or more fluid passageways may be provided radially inwards of the external handling surface.

The housing, optionally the main body, may comprise the one or more fluid passageways. Thus, a portion of the housing may comprise one or more fluid passageways which receive a flow of wetting fluid from the sealed container so as to direct the wetting fluid to an external surface of the catheter.

The one or more fluid passageways may be provided by and/or in fluid communication with the one or more piercing members. The piercing members may provide a portion of the fluid passageway. The fluid passageway may comprise one or more of a piercing member, a flow passage provided by the catheter outlet body and the housing. Thus, the fluid passageway may comprise a first portion provided by the piercing member, and a second portion provided by the housing and/or the catheter.

The one or more piercing members and/or fluid passageways may be tubular. The wall of the tube may be provided by a wall of the housing and/or the catheter.

The piercing member and housing and/or catheter may slidably engage with one another to provide the fluid passageway. Thus, the piercing member may comprise an outlet portion such as a nozzle which is slideably received within a corresponding fluid passageway portion of the catheter or housing.

The catheter assembly may further comprise: a sheath arranged around the catheter tube. The sheath may be a flexible retractable sheath. The sheath may provide a tether for retaining a retractable insertion guide provided at the insertion end of the catheter. The sheath may provide an enclosure for maintaining the sterility of the catheter tube during insertion, and/or for directing the wetting fluid towards the external surface of the catheter tube. The fluid passageways may be configured to direct wetting agent into a volume bounded by the sheath.

The cap may be removeable. Thus, the cap may be fully separated from the main body which houses the catheter. Removal of the cap may allow easier access to the proximal end of the catheter which is held by a user during insertion.

The cap may be configured to retain the sealed container when the cap is removed. Thus, the sealed container may be fixedly attached within the cap.

The sealed container and/or cap may be configured to retain the piercing member when in the second position such that the piercing member is removable with the cap. The piercing member may mate with a piercing portion of the sealed container. The piercing portion may be configured to grip the piercing member when pierced.

The cap may be configured to move towards the piercing member when the cap is moved from the first position to the second position. The movement may comprise an axial movement along the longitudinal axis of the catheter and/or housing.

The movement of the cap may be guided by a guide. The guide may be provided by a channel on one or other of the housing and cap, the channel slideably receiving and guiding a projection, e.g. a pin, formed on the other of the cap or housing. For example, an outer surface of the main body of the housing may comprise a channel with an inside surface of the cap comprising a pin which is received within the channel, or vice versa.

The channel may provide a bayonet fitting comprising a first portion configured to guide the cap from the first position to the second position; and optionally from the second position to a third position in which the cap is removed.

The channel may comprise a second portion; the second portion may be configured to guide the cap from the second position to the third position. The third position may correspond to removal of the cap.

The channel may comprise a third portion; the third portion connecting the first and second portions, wherein the third portion is configured to be traversed when the cap is rotated relative to the main body.

The piercing member may be axially located by the catheter. The piercing member may be axially restrained by the catheter in a proximal direction and axially unrestrained by the catheter in a distal direction.

In a further aspect, the present disclosure provides a method of preparing a catheter for use. The catheter may be any catheter as disclosed herein. The method may comprise: moving a cap of a catheter housing from a first position to a second position so as to pierce a sealed container of wetting agent with a piercing member; and directing the wetting agent from the pierced sealed container to an external surface of a catheter tube. Directing the wetting agent from the sealed container to the external surface of the catheter tube may comprise bypassing an external handling surface of the catheter. The piercing member may direct the wetting agent from the pierced sealed container to the catheter tube. The method may further comprise removing the cap following the wetting of the catheter tube, wherein removing the cap comprises removing the sealed container and, optionally, the piercing member, with the cap.

BRIEF DESCRIPTION OF THE DRAWINGS

In order that the invention may be more clearly understood one or more embodiments thereof will now be described, by way of example only, with reference to the accompanying drawings, of which:

FIG. 1 provides a longitudinal cross sectional view of a catheter assembly according to the present invention;

FIGS. 2a and 2b show a perspective view and longitudinal cross sectional view of a catheter which may form part of the catheter assembly of FIG. 1;

FIG. 3 shows a perspective view of a distal end of main body of the housing; and, FIGS. 4a to 4c show the stages of preparing a catheter for use, in particular, the wetting of the catheter tube with a wetting agent housed in a sealed container.

DETAILED DESCRIPTION OF THE INVENTION

In the following description, the terms distal and proximal are to be taken in relation to an insertion end of a catheter. Hence, the proximal end of the catheter relates to the insertion end of the catheter, and the distal end is that held by a user for the purpose of insertion. The terms forwards and rearwards are to be taken in relation to the proximal end being forwards, and the distal end being rearwards. References to axial and radial will be in reference to the longitudinal axis of the catheter, unless stated otherwise.

The present disclosure provides a catheter assembly. The catheter assembly comprises an external housing, a sealed container comprising a wetting agent and a piercing member for piercing the sealed container. Piercing the sealed container releases the wetting agent. Once released, the wetting agent is directed towards a catheter housed within the external housing so as to lubricate the catheter for use.

An embodiment of a catheter assembly can be seen in FIG. 1 which is described in detail below.

The piercing member may face rearwards and may be distal-most in relation to the catheter so as to project from a terminal end of the catheter. The sealed container is movable relative to the piercing member. Thus, the piercing member may be mounted in a stationary relation relative to the catheter with the sealed container configured to move towards the piercing member during a wetting phase. The relative movement of the piercing member and sealed container may be achieved when opening the external housing to expose the catheter for use.

In some embodiments, the sealed container may be located in a first part of the external housing which is separate to and movable relative to a second part of the external housing. The first part of the external housing may be a cap of the external housing. The second part of the external housing may be a main body of the external housing to which the cap is detachably attached prior to (and possibly after) use. Removing the cap by a user may cause the necessary relative movement between the sealed container and the piercing member. Removal of the cap may be defined by a piercing phase, in which the sealed container is pierced, a wetting phase, in which the wetting agent is directed towards the exterior of the catheter, and a removal phase, in which the cap is removed such that the catheter may be removed in preparation of the catheter being used.

In an embodiment, the cap may be displaced from a first pre-use/sealed position towards a main body prior to removal. The cap may be displaced sequentially from the first, sealed position, to a second, piercing position, to a third, removed position. The transition between the first and second, and second to third positions, may include movement along and/or about an actuation axis. The actuation axis may be aligned with the longitudinal axis of the catheter and may define a piercing direction in which the piercing member is configured to pierce the sealed container. Displacement between the first and second positions may correspond to the piercing phase, the second position may provide the wetting phase, and displacement between the second and third position may correspond to the removal phase.

An embodiment of an example catheter assembly undergoing a piercing phase, a wetting phase and a removal phase is shown in FIGS. 4a to 4c, which are described in detail below.

The displacement of the cap is typically done by hand and may be achieved with the assistance of one or more mechanical guides which direct the movement of the cap relative to the body during all or any of the piercing phase, wetting phase and removal phases. The mechanical guides may comprise, for example, a screw-thread or a bayonet type engagement between the cap and main body of the housing. Thus, the cap may be screwed towards the main body to effect the piercing of the sealed container prior to the cap being removed. Alternatively, the cap may be pushed towards the main body to effect the piercing of the sealed container during the piercing phase, prior to being pulled away from the main body during the removal phase. The actuation path may also include one or more intermediate steps such as a twist or rotation phase to transition between the piercing phase and removal phase. The intermediate steps may or may not comprise the wetting phase which may occur during or immediately after the piercing phase.

The mechanical guides may include one or more features in the form of channels, grooves, ridges, threads, etc, which can serve to reliably guide the travel path of the cap relative to the main body under a manual actuation.

An embodiment of an external housing cap is shown below in FIGS. 4a to 4c, which is described in detail below.

When in a sealed or pre-use state, the cap may be detachably attached to the main body in an axially displaced manner, such that the cap can be displaced towards the main body to effect the piercing whilst the internal volume of the external housing is maintained in a substantially sealed state. Thus, the external housing may be sealed prior to use, and also following the piercing and wetting phases. Hence, when the movement of the cap towards the body results in a displacement of the piercing member towards the sealed container and a release of the wetting agent, the wetting agent remains sealed within the external housing such that the catheter can be wetted without escape of the wetting agent. The wetting agent may be retained within the external housing or drained following the removal of the cap.

Either the piercing member or sealed container may be distal-most in relation to an insertion end of the catheter.

The sealed container and piercing member may be removed with the cap during the piercing phase or removal phase. For example, the piercing member may be retained within the sealed container following the piercing phase. Thus, once the piercing member has penetrated the sealed container, the sealed container and piercing member are unified such that moving the sealed container results in the piercing member being moved also.

Prior to use, the piercing member may be attached to the main body of the external housing or a distal end of the catheter. The attachment may allow movement of the piercing member axially away from the catheter but prevent movement towards the catheter during the piercing phase. Hence, the piercing member may be prevented from moving away from the sealed container and cap during the piercing phase and free to move away from the catheter during the removal phase.

The piercing member and/or catheter may comprise one or more flow directing features configured to direct the flow of the wetting agent towards the catheter during the wetting phase. The flow directing features may include one or more conduits arranged in flow communication with the internal volume of the sealed container in which the wetting agent is stored, and to provide a flow path, which may be provided by a pipe, tube, passage or channel between the internal volume of the sealed container and the catheter. The one or more conduits may be provided by or referred to herein as wetting agent fluid or flow passageways.

The fluid passageways may bypass an outlet of the main catheter tube so as to provide a passage from the distal side of the catheter to an external surface of the catheter tube which provides a sliding contact with the urethra during insertion. The bypassing flow path may be referred to as a bypass channel.

The catheter may comprise an external handling surface. The external handling surface may be provided at a distal end of the catheter and provided by an outlet body of the catheter. The fluid passageways may bypass the external handling surface such that the external handling surface does not come into contact with the wetting agent.

The external surface of the catheter may be provided in a wetting zone which exists between an inner wall of the external housing and an external surface of the catheter tube.

The flow path may comprise the piercing member and the catheter. The piercing member and catheter may comprise one or more conduits in flow series which extend between the sealed container and the wetting zone in which the catheter resides within the external housing. The wetting zone may be defined by an internal surface of the external housing, or a sheath which surrounds a portion of the catheter.

The sheath may be a retractable sheath. The retractable sheath may be configured to be retracted during insertion of the catheter such that it provides a temporary enclosure around the catheter tube prior to insertion to aid with the wetting phase. The sheath may also provide a restraint for a retractable insertion guide which is provided at the proximal end of the catheter towards the insertion end and used to locate the catheter tube at the entrance to the urethra.

The catheter may include an outlet at the distal end thereof. The outlet may include one or more formations to aid the outflow of urine during use, such as funnel-like structure which diverges along the flow direction. The catheter outlet may include one or more conduits which provide a portion of the flow path for directing the flow from the sealed container to the catheter tube during the wetting phase. The one or more catheter flow path conduits may include an inlet and an outlet with a passage therebetween. The passage may be defined by a conduit wall which is provided as part of or within a wall of the catheter outlet.

The catheter outlet may comprise at least a main flow passage along which urine passes during use. The main flow passage extends from the catheter inlet at the insertion end to the catheter outlet at the distal end. Thus, the main flow passage for the catheter is provided by and is internal to the catheter tube. The wetting flow path(s) may extend from the catheter outlet to an exterior of the catheter tube. The main flow passage and wetting agent fluid passageway may be provided with an outlet body of the catheter. The fluid passageway and main flow passage may both extend axially along the length of the catheter. The wetting agent fluid passageways may be radially outside of the main flow passage.

The piercing member may comprise one or more lances which extend from the catheter outlet towards the sealed container. The one or more lances may be defined by a piercing end which penetrates the sealed container, and a fixed end which attaches the lance to body of the piecing member. The lance may be hollow so as to provide a portion of the one or more conduits which make up the wetting flow path between the sealed container and the outlet of the catheter. Where there is a plurality of lances, the lances may be arranged on diametrically opposing sides of the longitudinal axis of the catheter. There may be one, two, three or more lances and associated flow paths.

The piercing member may include one or more outlet tubes. The piercing member outlet tubes may be attached to and/or slidably received within the catheter outlet. The piercing member outlet tubes may be slidably received within the catheter corresponding passages in a telescopic manner. The corresponding passages may form part of the one or more conduits which direct the wetting fluid from the sealed container to the catheter.

FIG. 1 shows a longitudinal cross section of a catheter assembly 10. The catheter assembly 10 comprises an external housing 12, a sealed container 14 comprising a wetting agent 16 and a piercing member 18 for piercing the sealed container 14. Piercing the sealed container 14 releases the wetting agent 16. Once released, the wetting agent 16 is directed towards a catheter 22 housed within the external housing 12 so as to lubricate the catheter 22 for use.

The external housing comprises a cap 24. In the illustrated embodiment of FIG. 1, the cap 24 is shown as comprising the sealed container 14 of wetting agent 16. The cap 24 may be configured to move from a first, sealed, position (an example of which can be seen in FIG. 4a) to a second, piercing, position (an example of which can be seen in FIG. 4b). When in the second position the piercing member 18 is configured to pierce the sealed container and direct the wetting agent to an exterior surface of the catheter tube 28.

The wetting agent 16 may be any suitable fluid for lubricating the catheter tube 28 such as water.

The external housing 12 (which may be referred to as a housing for convenience) comprises a main body 30 in which a portion of the catheter 22 is housed, and the cap 24 which is detachable so as to be removed by a user prior to use, so that the catheter 22 can be withdrawn from the housing 12.

The housing 12 provides an enclosed space in which the catheter 22 can be housed for storage and transportation prior to use. The housing 12 is generally elongate having a longitudinal axis 32 which is coaxially arranged with the longitudinal axis of the catheter tube 28. The enclosed space is defined by an external wall of the housing 12 which extends from a first proximal end which receives the insertion end 34 of the catheter 22, to a second distal end in which a catheter outlet end 36 is received. In the embodiment shown, the second end is provided by the cap 24. Thus, the removal of the cap 24 exposes the outlet end 36 of the catheter 22 such that a user can grip and remove the catheter 22 from the housing 12 for use.

The external profile of the housing 12 can be any required for aesthetic or practical purposes and, in the example shown, is generally cylindrical, tapering towards the first end to aid insertion into a storage receptacle or pocket, for example, and tapering towards the second end along the length of the cap 24.

The cap 24 comprises an open-ended generally cylindrical enclosure having a circumferential external wall which extends coaxially along the longitudinal axis 32, and a radially extending, axially facing end wall which provides a closed end at the terminal end of the cap 24 and housing 22. The cap 24 mates with the distal end of the main body 30 of the housing 12, such that the main body is received within an open end of the cap 24. However, it will be appreciated that the cap 24 could be received within an open end of the main body in some embodiments.

The cap 24 is movable in relation to the main body 30. When in the first position as shown in FIG. 1, the cap 24 is axially displaced from the main body 30 such that the cap 24 and main body 30 can be moved towards each other. The movement of the cap 24 towards the main body 30 causes the piercing member 18 to move rearwards and pierce the sealed container 14 thereby releasing the wetting agent 16 for directing to the exterior of the catheter tube 28.

When in the first position, the housing 12 provides a sealed enclosure which prevents ingress of fluid and maintains a sterile environment for the catheter 22. Further, the mating of the cap 24 to the main body 30 is such that, when the cap 24 is moved into the second position, the housing 12 may remain sealably intact sufficient for the wetting agent to be retained within the housing 12.

The attachment between the cap and main body may be provided by any suitable connection such as a push fit, screw cap or bayonet-type of attachment, for example. An embodiment of the cap attachment is described in more detail below in relation to FIG. 3.

To remove the cap 24, it is displaced from the first, storage, position as shown in FIG. 1, towards the main body 30. The movement of the cap 24 may be along a piercing or actuation axis which is coincident with the longitudinal axis 32 of the housing 12 and/or catheter tube 22. Hence the cap 24 and main body 30 are configured to move axially towards each other or away from each other during a wetting procedure.

The sealed container 14 is provided in the form of a capsule which is located within the cap 24, adjacent to and optionally abutting the axially facing end wall of the cap 24. Hence, the sealed container 14 is prevented from moving rearwards/distally away from the insertion end 34 and held in a fixed relation to the cap 24 such that it can be pierced by the piercing member 28 when the cap 24 and main body 30 are moved together. The sealed container 14 may be friction fitted or adhered to the cap 24, or attached by some other means. Fixedly attaching the sealed container 14 to the cap 24, allows the sealed container 14 to be retained within the cap 24 when the cap 24 is removed from the main body 30.

The sealed container 14 comprises one or more external walls which define an enclosed volume in which the wetting agent 16 is sealably contained so as to prevent escape prior to being pierced by the piercing member 18. The sealed container 14 may comprise a piercing portion 38 for piercing by the piercing member 18 in use. The piercing portion 38 in the embodiment shown in FIG. 1 is provided by an axially facing wall of the sealed container 14 which faces distally towards the insertion end 34 of the catheter, along the piercing axis 32. Thus, the piercing portion 38 is located in the path of the rearward facing piercing member 18 when the cap 24 and main body 30 are moved toward one another.

The piercing member 18 is located proximally of the sealed container 14 and static in relation to the movement of the cap 24 when the cap 24 travels along the piercing axis 32. Thus, when the cap 24 is moved along the piercing axis 32, the piercing member 18 and sealed container 14 move toward one another to provide a piercing movement.

The piercing member 18 shown in FIG. 1 is provided adjacent and distal to the outlet end of the catheter tube 28 so as to provide a rearward facing projection. The piercing member 18 may comprise one or more lances 18a, 18b which extend distally away from the outlet end of the catheter tube 28 towards the sealed container 14. The lances 18a,b may be supported by and extend from a piercing member body 18c to a tip which faces the piercing portion 38. The tip may be suitably shaped to allow a piercing action. For example, the tip may be pointed and/or sharpened to provide a piercing/cutting edge.

The piercing member 18 is restrained from movement in a first direction but may be movable in a second direction. Thus, during a piercing phase, the piercing member 18 may be restrained so as to resist being moved by the sealed container 14 when urged into the piercing member 18. As such, the piercing member 18 may pierce the piercing portion 38 upon application of a suitable force. The piercing member 18 may be movable in a second direction such that, following the piercing of the sealed container 14, the piercing member 18 may be retained by the sealed container 14 such that it is removed with the cap 24 as the cap 24 and main body 30 are separated. The retention of the piercing member 1 may be achieved by the piercing portion 38 being made from a suitably resilient material which can friction grip the piercing member 18, for example. It will be appreciated that in some embodiments the piercing member may be removed separately from the cap 24.

Although not clearly shown in FIG. 1, the piercing member 18 may be separate part which is separately inserted into the housing 12 during the assembly of the catheter assembly 10. Thus, the piercing member 18 may be a separate component and not one which is integrally formed with the housing or catheter. It will be appreciated from the description herein that the insertion of the piercing member 18 into the housing may comprise inserting into or otherwise attaching it to the catheter 22, or, in some embodiments, to the housing directly.

The piercing member 18 may be formed from a different material to that of the housing 12 and cap 24; for example, a metal, e.g. steel, such as surgical steel may be more suitable for the piercing member, whilst a plastic, e.g. a thermoplastic such as polypropylene, or alternatively as polycarbonate, polyethylene, or nylon may be more suitable for the housing 12 and cap 24.

The piercing member 18 comprises a body 18c which may be in the form of a plate shaped member or flange which lies in the normal plane of the longitudinal axis 32. The piercing projections, e.g. lances 18a and 18b, extend from the distal side of the piercing member body 18c parallel to the piercing axis 32. The proximal side of the piercing member body 18c provides a location feature which can abut a corresponding surface of the housing or catheter 22, such as the distal end of the catheter outlet thereby defining the axial location of the piercing member 18 within the housing 12.

The piercing member 18 may include one or more conduits, i.e. fluid passageways, for directing the wetting agent 16 from the sealed container 14 towards an external surface of the catheter tube 28. As shown in FIGS. 1, 2a and 2b the fluid passageways may be provided in part by the lances 18a,b. Thus, the or each lance 18a,b may be hollow so as to include an internal passage which provides a flow path from the interior of the sealed container 14 to an exterior of the sealed container 14 and directed towards the exterior of catheter tube 28. The fluid passageways may have an inlet provided within the sealed container 14 when pierced, and an outlet which is located in fluid communication with the external surface of the catheter tube 28. The or each fluid passageway outlet may be provided within the main body 30 of the housing 12 and, when present, in a retractable sheath 40 which surrounds the catheter tube 28. By providing two fluid pathways, one of the pathways may act as a venting channel. Thus, wetting agent 16 may flow through both fluid passageways, or the wetting agent may flow through one passageway, whilst gas (e.g. air) from within the housing 12 flows through the other passageway to displace the wetting agent. Alternatively, a separate venting channel could be provided, or it may operate without a venting channel, for example, pushing and twisting the cap would pierce and force water out of the capsule. The water volume released from the capsule would be replaced in the cap by air from the enclosure, passing up through the catheter drainage lumen. The air would then escape to the outside.

The wetting agent fluid pathway may be provided entirely by the one or more lances 18a,b, or may comprise a plurality of sections provided by different parts of the catheter assembly. Thus, for example, as shown in the embodiment of FIGS. 1, 2a and 2b, fluid passageways which make up the wetting agent fluid pathway may be provided by one or more of the piercing member 18 and the catheter 22.

Optionally, the piercing member 18 may include one or more projections which extend from the proximal surface of the piercing member body 18c. The one or more projections may be in form of pins and may include part of the fluid passageways for directing the wetting agent 16 from the sealed container 14 to the catheter 22. The projections may also provide additional location features for axially and angularly locating the piercing member 18 in the catheter 22.

As can be seen in FIG. 4c, the projections may be provided in the form of outlet tubes 18d,e, or nozzles, which are an extension of the flow passages provided by the lances 18a,b. The outlet tubes 18d,e may be received by corresponding portions of the catheter 22, an example of which is provided below in connection with FIGS. 2a and 2b or a housing wall of the main body 30 (not shown).

FIGS. 2a and 2b show an embodiment of a catheter 222. FIG. 2a shows a perspective view of the catheter 222, with FIG. 2b showing a longitudinal section taken along the longitudinal axis 332. The catheter 222 includes a catheter tube 228 which is insertable into a patient's urethra so as to enter the bladder and provides a main fluid path for urine to exit the body. The catheter tube 228 includes a first end 234, which may be referred to as an insertion end, and a second end 236, which may be referred to as an outlet end. The main fluid path of the catheter 222 is provided by a fluid passageway/conduit defined by a wall of the catheter tube 228 which extends longitudinally between the first end 234 and second end 236. The transverse cross section of the catheter tube 238 is typically round to provide a cylindrical catheter tube 228, although other shapes may be possible. The longitudinal axis 332 of the catheter tube 228 defines the principal longitudinal axis of the catheter 322.

The second, outlet end 236 of the catheter 222 may include a catheter outlet body 242. The catheter outlet body 242 comprises an external outer surface which is formed so as to provide a handle for a user to grip during insertion and removal of the catheter 222 from the housing 22 and patient in use. Thus, the external outer surface may be an external handling surface.

An internal inner surface of the catheter outlet body 242 provides the terminal end of the main fluid passageway and comprises a funnel-like formation for assisting with or directing the flow of exiting urine. Thus, as seen in FIG. 1, the outlet end 236 of the catheter tube 238 may include a flared portion in which the internal diameter of the catheter tube 238 diverges along the flow direction to provide a funnel-like structure. It will be appreciated that the terminal end of the main fluid passageway may vary and may not be funnel shaped in some embodiments.

The insertion end 234 of the catheter tube 238 comprises an inlet for receiving the flow of urine into the main fluid passageway of the catheter tube 238 for transporting to the catheter tube outlet end 236. The inlet may be provided by one or more apertures in the catheter tube wall. The inlet is not shown in the Figures, but inlets are well known in the art. The terminal end of the catheter may also be provided with a rounded profile (or bull nose formation) to aid insertion and patient comfort.

As can be seen best in FIGS. 2a and 2b, the outlet end 236 may comprise one or more conduits 244a,b which may receive corresponding parts of the piercing member 18, such as the outlet tubes 18d,e shown in FIG. 4c. The one or more conduits 244a,b may provide a portion of the fluid passageways for directing the wetting agent 16 from the sealed container 16 to the exterior of the catheter tube 238. Thus, as shown in FIG. 2b, the wetting agent fluid passageway is provided by a tubular member which extends from an inlet end provided at the terminal end of the catheter outlet body 242 which is configured to receive fluid from the sealed container 14, to an outlet end which is located radially outwards of the catheter tube 238. As such, when wetting agent fluid flows from the sealed container 14 along the passageway, it exits onto the external surface of the catheter tube 228, as indicated by the arrow 246. It will be appreciated that a similar fluid path may be provided by passageway 244a.

As can be seen, the wetting agent fluid passageways 244a,b are radially outside of the main fluid passageway provided by the catheter tube 238 and bypass the outlet of the main fluid passageway. Hence, the wetting agent fluid passageways 244a,b may be referred to as bypass channels. More generally, the bypass channels may comprise a first end which opens on a distal side of the catheter outlet and terminate on a proximal side of the catheter outlet, thereby bypassing the main flow path outlet and external handling surface and extending to an exterior of the catheter tube from the outlet side.

Returning to FIG. 1, there is shown an optional catheter insertion guide 48 which can be used by the user to locate the insertion end 34 at the entrance to the urethra. The insertion guide 48 (which may be referred to as a gripper) may be an annular member located radially outwardly of the catheter tube 38. The radially outer surface is configured to be grippable by a user's fingers and may include one or more surface features, such as the annular grooves shown in FIGS. 1, 2a and 2b for improving grip and user dexterity. The insertion guide 48 is generally elongate with a longitudinal axis which is co-axial with the longitudinal axis 32 of the catheter tube 38.

The insertion guide 48 is configured to remain external to the urethra when the catheter tube 38 is inserted and so is retractable. Hence, the catheter tube 38 can pass through the insertion guide 48 such that the insertion guide 48 moves rearwards to towards the outlet end during insertion. When fully retracted, the insertion guide may abut the proximal end of the catheter outlet body 42.

FIGS. 1, 2a and 2b also shown an optional retractable sheath 40 located radially outside of the catheter tube 38. The sheath 40 extends from an attachment on the catheter outlet body 42 to an attachment on the insertion guide 48 and provides an enclosed space in which the catheter tube 38 is located. The sheath 40 is flexible and retractable with the insertion guide 48. Hence, when the insertion guide 48 is in the pre-insertion position the sheath 40 is in an extended unfurled state (as shown in FIG. 1), and when the positioning aid is in the retracted post-insertion position, the sheath 40 is bundled in a furled/concertinaed manner towards the second outlet end of the catheter tube. The sheath 40 may provide an enclosed space for controlling the distribution of the wetting fluid 16, and/or, providing a mechanical connection, i.e. a tether, between the insertion guide 48 and the outlet body, such that insertion guide 48 can be withdrawn from the housing 12 with the catheter 22. The sheath 40 may additionally or alternatively, provide a sterile environment for the catheter tube 28 immediately prior to insertion.

FIG. 3 shows an embodiment of a distal end of a main body 330 of a housing comprising a guide 350 which determines the actuation path of a cap 24 when moving between the first and second positions to instigate the piercing phase, wetting phase and removal phase of the removable cap 24. Although the distal end of the main body 330 is shown, it will be appreciated that the guide channel 350 shown in FIG. 3 and described below may be provided by the removable cap 24.

As previously described the main body 312 comprises an open distal end in which the catheter (not shown) is received. A first wall portion 352 extends proximally away from the distal end, and a second wall portion 354, extends from the first wall portion 352 to the proximal, insertion end of the of the housing 12. The first wall portion 352 has a reduced radius compared to the second wall portion 354 so as to be narrower such that it can be received within the cap 24. It will be appreciated that the differing diameters of the first wall portion 352 and second wall portion 354 is an optional feature which allows the outer surface of the main body 330 and cap 24 to be consistent along the length of the housing 12. In some embodiments, the distal end of the main body 330 may comprises a continuous diameter.

The cap 24 may be used to actuate the piercing of, and release of the wetting agent from, the sealed container shown in FIG. 1. To enable this, the cap 24 and main body 330 comprise an interlock which directs the actuation of the cap 24 along an actuation path. As such, the main body 330 (or cap 24) may comprise one or more guides 350 which are used to control the movement of the cap 24 along an actuation path. The actuation path may involve movement of the cap 24 from a first, pre-use position in which the sealed container 14 remains in-tact, to a second, piercing or pierced position, in which the sealed container 14 is pierced by the piercing member 18. The actuation path may involve movement of the cap 24, from the second, piercing position, to a third removal position in which the cap 24 is removed from the main body 330. Thus, the actuation may comprise push-pull type action in which the cap 24 is urged towards the insertion end and piercing member, prior to be being urged rearwards, i.e. pulled, to remove it.

With reference to FIG. 3, the cap 24 and main body 330 may comprise a bayonet attachment comprising an actuation path provided by a guide channel 350 which extends from an axial mid-portion of the first wall portion 352 located between the distal end of the main body 330 and the proximal end of the first wall portion 352, to the proximal end of the first wall portion 352 along the direction of the longitudinal axis 32, extends circumferentially about the first wall portion 352 around the longitudinal axis 32, prior to returning to an open end at the terminal end main body 330 to provide an open-ended channel. The guide channel 350 engages with a corresponding runner in the form of a projection, such as a pin, which extends from an internal surface of the cap 12 which is slidably received within the guide channel 350.

Thus, as shown, the guide may comprise a guide channel 350 comprising a first, axially extending section 350a, a second angular section 350b and a third axial section 350c from which the guide pin exits to allow removal of the cap.

The first portion 350a corresponds to the piercing phase where the cap 24 is moved from the first position to the second position, the second portion 350b represents a rotation of the cap which positions the cap 24 in a withdrawal position at the entrance of the third portion. The wetting phase may occur during any or all of the portions following a piercing of the sealed container 14 and prior the removal of the cap 24, or the sealed container 14 being drained.

FIGS. 4a to 4c show the actuation steps required to wet the catheter 22 and release the cap 24 in use. FIG. 4a shows a longitudinal section of the catheter assembly 10 which corresponds to FIG. 1 with the same reference numerals denoting corresponding features which will not be described further. FIG. 4b shows the catheter assembly 10 following the wetting phase in which the cap is moved proximally towards the insertion end during a wetting phase in which the wetting agent is directed towards the exterior of the catheter tube 22. FIG. 4c shows the cap 24 removed following the wetting phase and removal phase in which the cap 24 is moved distally rearwards so as to become disengaged from the body.

Thus, in FIG. 4a there is shown a catheter assembly 10 comprising an external housing 12, a sealed container 14 comprising a wetting agent 16 and a piercing member 18 for piercing the sealed container 14. Piercing the sealed container 14 releases the wetting agent 16. Once released, the wetting agent 16 is directed towards a catheter 22 housed within the external housing 12 so as to lubricate the catheter 22 for use.

The external housing comprises the cap 24 comprising the sealed container 14 of wetting agent 16. The cap 24 is configured to move from a first, sealed, position to a second, piercing, position shown in FIG. 4b. When in the second position the piercing member 18 is configured to pierce the sealed container 14 and direct the wetting agent to an exterior surface of the catheter tube 28 via wetting agent flow passages provided by conduits in the piercing member and, in this embodiment, the outlet end of the catheter 22. Following the wetting of the catheter tube 28, the cap 24 can be removed, as shown in FIG. 4c and disposed of or retained for placing back on the main body following a reinsertion of the catheter 22 once used. Once the cap 24 has been initially removed, the catheter 22 may be gripped by the distal outlet end body 42 and inserted into a urethra, using the optional insertion guide 42 where present, to manoeuvre the end into the correct position. Once in the correct location at the entrance to the urethra, the catheter tube 28, lubricated with the wetting agent 16, may be inserted into the urethra through the insertion guide 42 such that the outlet end approaches the insertion guide 42 until the catheter tube 28 is sufficiently inserted. Following use, the catheter may be withdrawn and placed back in the housing for disposal.

The one or more embodiments are described above by way of example only. Many variations are possible without departing from the scope of protection afforded by the appended claims.

The invention claimed is:

1. A catheter assembly comprising:
a cap containing a wetting agent;
a catheter having a catheter tube and an outlet end; and
a piercing member;
wherein the catheter assembly comprises at least one fluid passageway configured to direct the wetting agent to an external surface of the catheter tube bypassing an exterior handling surface of the outlet end of the catheter;
wherein the catheter comprises an outlet body, wherein the outlet body comprises at least part of one main flow passage for passage of urine;
wherein the outlet body further comprises the at least one fluid passageway.

2. The catheter assembly of claim 1, comprising an external housing, the external housing comprising the cap.

3. The catheter assembly of claim 1, wherein the cap comprises a sealed container of wetting agent.

4. The catheter assembly of claim 1, wherein the piercing member comprises the at least one fluid passageway.

5. The catheter assembly of claim 4, wherein the at least one fluid passageway is arranged radially outwardly of the main flow passage.

6. The catheter assembly of claim 1, wherein the at least one fluid passageway is integrally formed in the outlet body of the catheter.

7. The catheter assembly of claim 1, wherein the at least one fluid passageway is tubular.

8. The catheter assembly of claim 1 wherein the piercing member is slidably received by the outlet end of the catheter to provide a portion of the fluid passageway.

9. The catheter assembly of claim 1, further comprising a sheath arranged around the catheter tube.

10. The catheter assembly of claim 9, wherein the at least one fluid passageway is configured to direct wetting agent into a volume bounded by the sheath.

11. The catheter assembly of claim 1, wherein the cap is configured to move distally towards the catheter when moving from a first position to a second position.

12. A catheter assembly comprising:
a cap containing a wetting agent; and
a catheter having a catheter tube and an outlet end;
wherein the catheter assembly comprises at least one fluid passageway configured to direct the wetting agent to an external surface of the catheter tube bypassing an exterior handling surface of the outlet end of the catheter;
wherein the catheter comprises an outlet body, wherein the outlet body comprises at least part of one main flow passage for passage of urine;
wherein the outlet body further comprises the at least one fluid passageway;
wherein an external housing further comprises a main body to which the cap is detachably attached.

13. The catheter assembly of claim 12, wherein the catheter tube is at least partially arranged within the main body.

14. The catheter assembly of claim 12, wherein the main body comprises the at least one fluid passageway.

15. The catheter assembly of claim 12, further comprising a guide for guiding the movement of the cap between a first position and a second position, wherein the guide comprises a pin formed on the inside of the cap and a corresponding channel arranged on the outside of the main body.

16. The catheter assembly of claim 15, wherein the channel comprises a first portion configured to guide the cap from the first position to the second position; and optionally, from the second position to a third position, wherein the third position provides access to the catheter outlet.

17. The catheter assembly of claim 16, wherein the channel comprises a second portion configured to guide the cap from the second position to the third position.

18. The catheter assembly of claim 17, wherein the channel comprises a third portion; the third portion connecting the first and second portions, wherein the third portion is configured to be traversed when the cap is rotated.

19. A catheter assembly comprising:
a cap containing a wetting agent; and
a catheter having a catheter tube and an outlet end;
wherein the catheter assembly comprises at least one fluid passageway configured to direct the wetting agent to an external surface of the catheter tube bypassing an exterior handling surface of the outlet end of the catheter;
wherein the catheter comprises an outlet body, wherein the outlet body comprises at least part of one main flow passage for passage of urine;
wherein the outlet body further comprises the at least one fluid passageway;
wherein the cap is removable, wherein the cap is configured to retain a sealed container when removed.

* * * * *